(12) United States Patent
Meili (10) Patent No.: US 11,819,819 B2
(45) Date of Patent: Nov. 21, 2023

(54) NITRATION REACTOR AND METHOD

(71) Applicant: NORAM INTERNATIONAL LIMITED, Dublin (IE)

(72) Inventor: Stefan F. Meili, North Vancouver (CA)

(73) Assignee: NORAM INTERNATIONAL LIMITED, Dublin (IE)

( * ) Notice: Subject to any disclaimer, the term of this patent is extended or adjusted under 35 U.S.C. 154(b) by 564 days.

(21) Appl. No.: 17/260,414

(22) PCT Filed: Nov. 15, 2018

(86) PCT No.: PCT/IB2018/059008
§ 371 (c)(1),
(2) Date: Jan. 14, 2021

(87) PCT Pub. No.: WO2020/021323
PCT Pub. Date: Jan. 30, 2020

(65) Prior Publication Data
US 2021/0260560 A1    Aug. 26, 2021

Related U.S. Application Data

(60) Provisional application No. 62/712,621, filed on Jul. 31, 2018, provisional application No. 62/702,664, filed on Jul. 24, 2018.

(51) Int. Cl.
*B01J 19/24*    (2006.01)
*B01J 10/00*    (2006.01)
(Continued)

(52) U.S. Cl.
CPC ......... *B01J 19/245* (2013.01); *B01J 10/002* (2013.01); *B01J 19/006* (2013.01); *C07C 201/08* (2013.01);
(Continued)

(58) Field of Classification Search
CPC ...... B01J 19/245; B01J 10/002; B01J 19/006; B01J 2219/185; B01J 2219/1941; C07C 201/08; C07C 205/06
See application file for complete search history.

(56) References Cited

U.S. PATENT DOCUMENTS 4,994,242 A    2/1991    Rae et al.
5,313,009 A    5/1994    Guenkel et al.
(Continued)

FOREIGN PATENT DOCUMENTS

CN    101489659 A    7/2009
WO    2008012520 A    1/2008

OTHER PUBLICATIONS

Trebilcock et al., "Assessment of Chemical Reactivity Hazards for Nitration Reactions and Decomposition of Nitro-Compounds," American Chemical Society, 2013, 19 pages.
(Continued)

*Primary Examiner* — Jafar F Parsa
(74) *Attorney, Agent, or Firm* — NYEMASTER GOODE, P.C.

(57) ABSTRACT

A nitration reactor (10) incorporating sections of downward flow for use in preparing nitrated organic compounds. It comprises a first vertically-oriented reactor section (12), a second vertically-oriented reactor section (14), a connecting section (16) between the two reactor sections, one or more inlets (20, 22) for introducing nitration reactants into the reactor, an outlet (24) for the removal of nitration reaction products, a vertically-downward flowpath (26) for the nitration reactants in one of the reactor sections or the connecting section, and operating conditions that produce a flow regime in the vertically-downward flowpath that is a dispersed flow regime or a bubbly flow regime. The invention overcomes the limitations of prior art nitration reactors of the type in
(Continued)

which fluids flow largely in a vertically upward direction, with respect to hydrostatic demands and plant layout considerations.

22 Claims, 4 Drawing Sheets

(51) Int. Cl.
    *B01J 19/00*     (2006.01)
    *C07C 201/08*     (2006.01)

(52) U.S. Cl.
    CPC ............ *B01J 2219/00777* (2013.01); *B01J 2219/185* (2013.01); *B01J 2219/1941* (2013.01)

(56) References Cited

U.S. PATENT DOCUMENTS

| | | |
|---|---|---|
| 5,616,818 A | 4/1997 | Pirkl et al. |
| 6,506,949 B2 | 1/2003 | Gillis et al. |
| 7,763,759 B2 | 7/2010 | Knauf et al. |
| 8,357,827 B2 | 1/2013 | Manning et al. |
| 8,592,637 B2 | 11/2013 | Denissen et al. |
| 8,604,256 B2 | 12/2013 | Berretta et al. |
| 8,692,035 B2 | 4/2014 | Berretta |
| 8,907,144 B2 | 12/2014 | Gattrell |
| 2011/0028731 A1* | 2/2011 | Trauth ............ C07D 263/04 548/215 |

OTHER PUBLICATIONS

Zalvidar et al. "Aromatic nitrations by mixed acid. Fast liquid-liquid reaction regime", Chem. Eng. Proc., 35 (1996) 91-105.

Crawford et al., 'Two-Phase Flow Patterns and Void Fractions in Downward Flow Part 1', Int. J. Multiphase Flow, vol. 11, No. 6 pp. 761-782, 1985.

Patent Cooperation Treaty, "International Search Report & Written Opinion," issued in connection with International Patent Application No. PCT/IB2018/059008, dated Jan. 25, 2019, 12 pages.

* cited by examiner

NITRATION REACTOR AND METHOD

FIELD OF THE INVENTION

The invention pertains to the nitration of aromatic organic compounds, and in particular to adiabatic plug-flow nitrators.

BACKGROUND OF THE INVENTION

Reactors for the adiabatic nitration of aromatic compounds are well known in the art. These reactors produce nitrated aromatic compounds by mixing sulphuric acid, nitric acid and one or more aromatic compounds to form a heterogeneous mixture of liquid phases, typically with the organic phase as the dispersed phase. A large volume of sulphuric acid is circulated through the reactor. The sulphuric acid acts as a catalyst, facilitating the dissociation of the nitronium ion from the nitric acid. The sulphuric acid also acts as a thermal mass into which the heat of reaction is absorbed. An aromatic compound such as benzene or toluene (or another) is introduced into the reactor. The aromatic reacts with the nitronium ion to produce a nitrated organic compound such as mononitrobenzene (MNB) or mononitrotoluene (MNT).

There currently exist three significant classes of adiabatic nitration reactors.

In the first class of reactor design, the reactor is oriented such that fluids flow largely in a vertically upward direction, and high pressure drop mixing devices are installed in it. The mixing devices are designed to produce fine dispersions of organic droplets, such as described in U.S. Pat. No. 4,994,242 (Rae). This type of reactor is typically operated according to the process conditions first disclosed in U.S. Pat. No. 5,313,009 (Guenkel), and once again in U.S. Pat. No. 8,357,827 (Munnig), but may alternatively be operated under conditions such as those disclosed in U.S. Pat. No. 8,604,256 (Berretta), U.S. Pat. No. 8,692,035 (Berretta) and U.S. Pat. No. 8,907,144 (Gattrell). Defining features of this class of reactor design are:

- More than half of the reactor volume is installed so that reactants flow in a vertically upward direction (i.e., inclined at more than 45°). Typically, short sections of horizontal flow are installed between upward flowing reactor sections so as to accommodate plant layout considerations.
- Mixing devices that produce intense turbulence are installed in vertically oriented sections of the reactor.
- The reactor is designed to produce plug flow with low back mixing throughout the reactor. Zones of especially low back mixing are typically installed in the first portion of the reactor.
- The reactors are capable of achieving nearly complete conversion of nitric acid to products, often achieving in excess of 99.99% conversion. See U.S. Pat. No. 8,357,827 (Munnig).

In the second reactor class, shearing mixing devices designed to mix partially phase separated reactants and installed between coalescing zones designed to partially phase separate the reacting fluids. This type of reactor was first disclosed in U.S. Pat. No. 6,506,949 (Gillis). Defining features of this class of reactor design are:

- More than half of the reactor volume is installed so that reactants flow in a generally horizontal orientation (i.e., inclined at less than 45°).
- Shearing mixing devices designed to mix partially phase separated reactants are installed in horizontally oriented sections of the reactor.
- The shearing mixing devices are installed between coalescing zones designed to partially phase-separate the reacting fluids.
- These reactors are unable to achieve a high degree of conversion, often achieving approximately 98.8% conversion of nitric acid to product. See U.S. Pat. No. 6,506,949 (Gillis).

The third class of nitration reactor, disclosed in U.S. Pat. No. 8,592,637 (Denissen), is similar to the second class of nitration reactor. In this type of design, plate type mixing devices are installed between back-mixed zones reactor zones. Vertically-oriented 180° bends installed between horizontal reactor sections are employed to increase conversion efficiency. Defining features of this class of reactor design are:

- More than half of the reactor volume is installed so that reactants flow in a generally horizontal orientation (i.e., inclined at less than 45°).
- Plate type mixing devices equipped with orifices or tabs are installed to mix the reactants in horizontal sections of the reactor.
- The plate type mixing devices are installed between highly back mixed reactor volumes. The reactors are designed such that zones of particularly high back-mixing exist in in the first portion of the nitration reactor.
- Vertically-oriented 180° return bends are installed between sections of horizontal flow, allowing this class of reactor design to achieve 98% conversion of nitric acid to product. See U.S. Pat. No. 8,592,637 (Denissen).

The first class of nitration reactor provides superior conversion of reactants to product. To achieve this high degree of conversion, the reactor must be arranged to generally flow upwards. The vertical orientation of the first class of reactor prevents bulk phase separation from occurring between mixing elements typical of horizontally oriented reactors and avoids the need for shear plate mixing devices which induce back-mixing.

Typically, nitration reactors are designed to allow complete separation and removal of the organic phase from the reactor by means of buoyant forces during a shutdown. This avoids the accumulation of reactants within the reactor during a shutdown, a scenario that is known to have caused a deflagration at a facility in Deepwater, NJ in 1967 ("*Assessment of Chemical Reactivity Hazards for Nitration Reactions and Decomposition of Nitro-Compounds*", R. W. Trebilcock & S. Dharmavaram, A C S 2013).

Nitration reactors should also be designed to allow for complete drainage during an extended shutdown for maintenance.

The first class of nitration reactor provides a superior degree of safety over competing designs as the organic phase can be quickly separated and removed from the reactor if acid circulation is lost. This design also allows quick and complete drainage of reactants for maintenance.

Reactors designed according to the second and third classes are horizontally oriented and accordingly drain much more slowly in the event of a loss of acid circulation. In these types of design, reactants are drained through small drain holes located at the bottom of the mixing elements in horizontal reactor sections. Once completely drained, more reactant residue is left in a horizontal reactor than in a vertical reactor.

The vertical design of the first class of nitration reactor often necessitates a tall and slender geometry. This design imposes larger hydrostatic demands on pumps circulating reactants than required by the second and third nitration reactor design classes. In order to deliver superior conversion of nitric acid and a superior degree of safety, a nitration plant employing the first class of reactor must be carefully laid out so as to accommodate the height and geometry of the reactor.

As discussed by Zaldivar, J. M.; Molga, E.; Alos, M. A.; Hernandez, H.; Westerterp, K. R. "*Aromatic nitrations by mixed acid. Fast liquid-liquid reaction regime*", Chem. Eng. Proc., 35 (1996) 91-105, and U.S. Pat. No. 8,907,144, the rate of reaction in the first class of nitration reactor is calculated:

$$\text{Rate} = \alpha x_{Ar} C_{Ar} \sqrt{k_{NAr} C_{HNO3} D_{Ar}}$$

where: Rate=rate of conversion of aromatic to nitroaromatic
$\alpha$=interfacial area
$C_{Ar}$=solubility of pure aromatic in the acid phase
$k_{NAr}$=rate constant of nitration of the aromatic
$C_{HNO3}$=bulk concentration of nitric acid
$D_{AR}$=diffusion coefficient of aromatic in acid phase.

According to this calculation, it is clear that the rate of conversion of the aromatic to nitroaromatic in the first reactor design class is proportional to the interfacial area generated between the aqueous acid phase and the organic phase. As a result, the ability of the first class of nitration reactor to convert an aromatic into a nitroaromatic is reduced if the reactant phases are allowed to coalesce and separate. Poor mixing is also known to favor the formation of byproducts such as dinitroaromatics, as disclosed in U.S. Pat. No. 8,907,144 (Gattrell).

Another key concern in the design of nitration reactors is the stability of two phase flow. Published investigations of two phase flow such as T. J. Crawford, C. B. Weinberger and J. Wesiman, '*Two-Phase Flow Patterns and Void Fractions in Downward Flow Part 1*', Int J. Multiphase Flow, Vol. 11, No. 6 pp. 761-782, 1985 generally categorize observed flow patterns as follows:

Stable 'Dispersed' or 'Bubbly' flow. Discrete, fine bubbles or droplets of the light phase significantly smaller than the pipe diameter are uniformly distributed throughout the continuous heavy phase and faithfully follow the bulk flow. A plug flow nitrator operating in this flow regime will perform excellently, as the surface area of the light phase generated by the mixing elements will remain high even at a significant distance from the last mixing element.

Chaotic, intermittent and transition flow regimes, typically described as 'Churn', 'Slug' or 'Plug' flow. Large accumulations of light phase are possible and high backmixing may occur. A nitration reactor operating under these conditions may be unsafe to operate due to possible accumulation of reactants, and would be expected to produce a higher proportion of byproducts due to back mixing.

Separated flow regimes typically described as 'Stratified', 'Annular' or 'Falling Film' flow. Large accumulations are guaranteed. A nitration reactor operating under these conditions is potentially unsafe to operate.

Clearly, it would be desirable to overcome the design limitations of the first class of nitration reactor with respect to hydrostatic height and plant layout by folding it back upon itself. However, this would necessitate sections of down-flow. Any such reactor concept would have to overcome the following difficulties. First, convolutions in the reactor volume create pockets in which reactants can accumulate in the event of a loss of circulation. Second, due to the action of buoyant forces, the light organic phase in a nitration reactor will tend to flow upwards in sections of bulk down-flow, slipping backwards relative to the bulk flow of the mixed acid phase. Slippage or back-flow of the organic phase relative to the bulk acidic phase in a nitration reactor could cause unstable transient behavior. This could result in buildup of organic phase in the down-flow sections during normal operation and affect the ability of the reactor to operate safely. It could also cause coalescence of the light phase into larger slugs and plugs, reducing reaction rate and therefore reducing conversion efficiency. It could also cause unstable flow and increase backmixing in the reactor, increasing byproduct formation.

The stability of two phase liquid-liquid downward flow cannot be reliably predicted from existing theory and is a highly experimental field of study. The literature relevant to this field is directed towards the characterization of vapour-liquid combinations in small diameter pipes used in heat exchangers boiling or condensing heat transfer media. No reference exists for liquid-liquid down-flow at an industrial scale relevant to a nitration reactor. For instance, see T. J. Crawford, C. B. Weinberger and J. Wesiman, '*Two-Phase Flow Patterns and Void Fractions in Downward Flow Part 1*', Int J. Multiphase Flow, Vol. 11, No. 6 pp. 761-782, 1985.

SUMMARY OF THE INVENTION

The present invention provides a plug-flow reactor incorporating sections of downward flow for use in the preparation of nitrated organic compounds such as MNB, MNT and other nitrated aromatic compounds, and methods of nitrating aromatic compounds using such reactors. The invention overcomes the limitations of the first class of nitration reactors with respect to hydrostatic demands and plant layout considerations while retaining the superior safety and nitric acid conversion efficiency characteristic of the first class of reactor.

One aspect of the invention provides a nitration reactor for use in nitrating aromatic organic compounds, comprising: (a) a first vertically-oriented reactor section; (b) a second vertically-oriented reactor section; (c) a connecting section between the first reactor section and the second reactor section for the flow of nitration reactants from the first reactor section to the second reactor section; (d) one or more inlets for introduction of the nitration reactants into the reactor; (e) an outlet for the removal of nitration reaction products from the reactor; (f) a vertically-downward flow-path for the nitration reactants in at least one of the first reactor section, the connecting section and the second reactor section; and (g) operating conditions that produce a flow regime in the vertically-downward flowpath that is a dispersed flow regime or a bubbly flow regime.

Another aspect of the invention provides a nitration reactor for use in nitrating aromatic organic compounds, comprising: (a) a first vertically-oriented reactor section; (b) a second vertically-oriented reactor section; (c) a connecting section between the first reactor section and the second reactor section for the flow of nitration reactants from the first reactor section to the second reactor section; (d) one or more inlets for introduction of the nitration reactants into the reactor; (e) an outlet for the removal of nitration reaction products from the reactor; (f) a vertically-downward flow-path for the nitration reactants in at least one of the first reactor section, the connecting section and the second reactor section; and (g) wherein operating conditions in the section of the reactor having the vertically-downward flowpath are such that a stability parameter Φ is in the interval of 0<Φ≤1, where $$\phi = \frac{\beta}{a \cdot \sqrt{Ri} + b \cdot Eo + c}$$

a=−1.1836×10⁻¹
b=2.2873×10⁻⁵
c=1.1904×10⁻¹
Ri=Richardson Number $$Ri = \frac{gD(\rho_c - \rho d)}{\rho_c U^2}$$

β=volumetric fraction of a dispersed, organic phase, $$\beta = \frac{Q_d}{Q_d + Q_c}$$

Eo=Eötvös Number $$Eo = \frac{(\rho_c - \rho_d)gD^2}{\sigma}$$

U=bulk fluid velocity $$U = \frac{Q_d + Q_c}{A}$$

D=downflow section hydraulic diameter $$D = \frac{4A}{P}$$

A=downflow section cross-sectional area,
P=downflow section cross-sectional perimeter,
g=gravitational acceleration constant,
$\rho_c$=density of continuous phase,
$\rho_d$=density of dispersed phase,
$Q_c$=volumetric flow of continuous phase,
$Q_d$=volumetric flow of dispersed phase, and
σ=interfacial tension.

Another aspect of the invention provides a method of nitrating an aromatic organic compound using a nitration reactor comprising a first vertically-oriented reactor section, a second vertically-oriented reactor section, a connecting section between the first reactor section and the second reactor section for the flow of nitration reactants from the first reactor section to the second reactor section, and a vertically-downward flowpath for the nitration reactants in at least one of the first reactor section, the connecting section and the second reactor section, the method comprising the steps of: (a) introducing the nitration reactants into the first reactor section; (b) flowing the nitration reactants through the first reactor section, the connecting section and the second reactor section under nitrating conditions to produce nitration products; (c) selecting operating conditions in the section of the reactor having the vertically-downward flowpath such that a flow regime in said section is dispersed flow or bubbly flow; and (d) removing the nitration products from the nitration reactor.

Another aspect of the invention provides a method of nitrating an aromatic organic compound using a nitration reactor comprising a first vertically-oriented reactor section, a second vertically-oriented reactor section, a connecting section between the first reactor section and the second reactor section for the flow of nitration reactants from the first reactor section to the second reactor section, and a vertically-downward flowpath for the nitration reactants in at least one of the first reactor section, the connecting section and the second reactor section, the method comprising the steps of: (a) introducing the nitration reactants into the first reactor section; (b) flowing the nitration reactants through the first reactor section, the connecting section and the second reactor section under nitrating conditions to produce nitration products; (c) selecting operating conditions in the section of the reactor having the vertically-downward flowpath such that a stability parameter Φ is in the interval of 0<Φ≤1, where $$\phi = \frac{\beta}{a \cdot \sqrt{Ri} + b \cdot Eo + c}$$

a=−1.1836×10⁻¹
b=2.2873×10⁻⁵
c=1.1904×10⁻¹
Ri=Richardson Number $$Ri = \frac{gD(\rho_c - \rho_d)}{\rho_c U^2}$$

β=volumetric fraction of a dispersed, organic phase, $$\beta = \frac{Q_d}{Q_d + Q_c}$$

Eo=Eötvös Number $$Eo = \frac{(\rho_c - \rho_d)gD^2}{\sigma}$$

U=bulk fluid velocity $$U = \frac{Q_d + Q_c}{A}$$

D=downflow section hydraulic diameter $$D = \frac{4A}{P}$$

A=downflow section cross-sectional area,
P=downflow section cross-sectional perimeter,
g=gravitational acceleration constant,
$\rho_c$=density of continuous phase,
$\rho_d$=density of dispersed phase,
$Q_c$=volumetric flow of continuous phase,
$Q_d$=volumetric flow of dispersed phase, and
α=interfacial tension;
and (d) removing the nitration products from the nitration reactor.

Further aspects of the invention and features of specific embodiments of the invention are described below.

DETAILED DESCRIPTION

In adiabatic nitration reactors having a section with vertically downward flow of the two phase reactants, four distinct flow regimes may be observed in the down-flow section. These are Dispersed flow, Bubbly flow, Churn flow and Annular flow. The applicant has experimentally determined that these observed flow regimes are relatively well characterized by three classic dimensionless parameters: Richardson Number (Ri), Void Fraction (β), and Eötvös Number (Eo). These parameters are defined as follows:

$$Ri = \frac{gD(\rho_c - \rho_d)}{\rho_c U^2}$$

$$\beta = \frac{Q_d}{Q_d + Q_c}$$

$$Eo = \frac{(\rho_c - \rho_d)gD^2}{\sigma}$$

$$D = \frac{4A}{P}$$

$$U = \frac{Q_d + Q_c}{A}$$

where: Ri=Richardson Number
β=dispersed phase volumetric fraction
Eo=Eötvös Number
U=bulk fluid velocity
D=hydraulic diameter
A=downflow section cross-sectional area
P=downflow section cross-sectional perimeter
g=gravitational acceleration constant
$\rho_c$=density of continuous phase
$\rho_d$=density of dispersed phase
$Q_c$=volumetric flow of continuous phase
$Q_d$=volumetric flow of dispersed phase, and
σ=interfacial tension However, it is difficult to reliably predict transition from stable 'Dispersed' and 'Bubbly' flow regimes to unstable 'Churn' and 'Annular' flow regimes using these three parameters.

A support vector machine (SVM) algorithm was used to separate desirable 'Dispersed' and 'Bubbly' flow regimes from unstable or unsafe 'Churn' and 'Annular' flow regimes. A new dimensionless parameter (Φ) was discovered based on the output of the SVM algorithm that allows the transition from unstable to stable flow regimes to be reliably predicted in a nitrator including extended regions of downward flow.

The parameter Φ is defined as:

$$\phi = \frac{\beta}{a \cdot \sqrt{Ri} + b \cdot Eo + c}$$

where: Φ=Stability Parameter $a = -1.1836 \times 10^{-1}$
$b = 2.2873 \times 10^{-5}$
$c = 1.1904 \times 10^{-1}$
Ri, Eo and β are as defined above.

Figure 3:
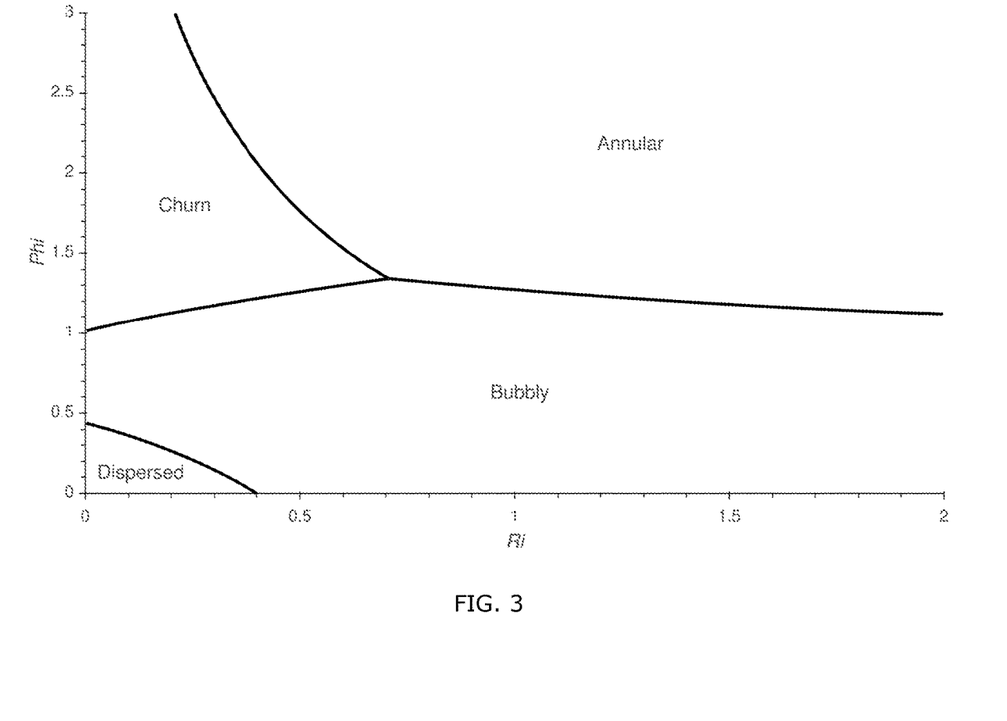
FIG. 3 is a graph showing flow regimes in a downward flow in the nitration reactor as related to the parameters Φ and Ri.

As shown in FIG. 3, transition from stable to unstable flow regimes can be predicted at approximately Φ=1, with Bubbly and Dispersed flow regimes occurring in the interval of 0<Φ≤1.

The four flow regimes observed in downward flowing sections of an experimental apparatus were found to be reliably predicted by two parameters: Richardson Number (Ri) and the stability parameter (Φ). The two stable flow regimes ('Dispersed' and 'Bubbly') are reliably predicted by the stability parameter alone.

As seen in FIG. 3, the dispersed flow regime exists at smaller values of the stability parameter (Φ). Indeed, the stability of two phase downward flow was observed to increase as the stability parameter was reduced towards zero. While stable two phase downward flow exists in the interval of 0<Φ≤1, it is preferred to design a nitration reactor incorporating sections of downward flow with smaller values of Φ. A more preferred embodiment of such a nitration reactor would operate with a stability parameter in the interval of 0<Φ≤0.75, and an even more preferred embodiment would operate with the stability parameter in the interval of 0<Φ≤0.5.

Surprisingly, the stability of the vertical down-flow sections is independent of the selection or location of the mixing devices installed in the up-flow section. It is clear that a reactor according to the present invention can be operated with any type of mixing device designed to create fine dispersions of light phase, without initiating unstable flow.

References in this disclosure to "vertically-oriented" reactor sections and "vertically-downward" flowpaths and the like means sections and flows that are at an angle of greater than 45 degrees. In practice, the sections and flows are substantially vertical. Likewise, references to "horizontal" sections and flows means sections and flows that are at an angle of less than 45 degrees. References to "reactor sections" includes ones with cross-sections that may be circular or non-circular or of arbitrary, regular cross-section, e.g., square, rectangular or polygonal.

Figure 1:
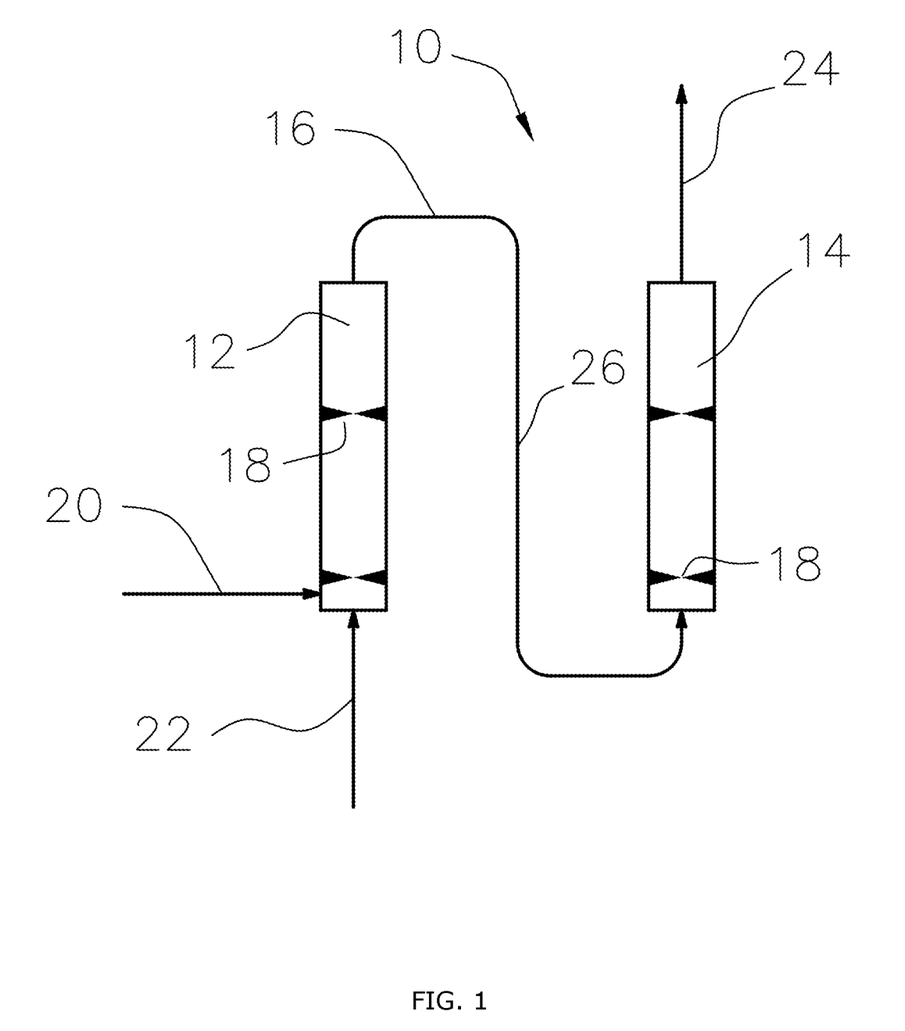
FIG. 1 is a schematic diagram of a nitration reactor according to one embodiment on the invention.

Referring to FIG. 1, which shows one embodiment of the invention, the nitration reactor 10 has a first vertically-oriented reactor section 12, a second vertically-oriented reactor section 14 and a connecting section 16 between the first reactor section and the second reactor section for the flow of nitration reactants from the first reactor section to the second reactor section. The connecting section 16 has a region 26 with a vertically-downward flowpath. The cross-section of the connecting section is preferably circular, i.e., the connecting section is a cylindrical conduit, but can be any regular cross-sectional shape, for example ellipsoidal, square, rectangular or polygonal. The two reactor sections 12, 14 are mounted at the same elevation. Mixing devices 18 are located in the sections 12, 14. Reactant inlets 20, 22 are located at the lower end of the first reactor section 12. For example, inlet 20 is for the introduction into the reactor of the organic phase and inlet 22 for the introduction of the aqueous, mixed acid phase. It will be apparent that the reactants may be introduced individually, which would require three separate inlets, or they may be previously mixed, requiring only one inlet, or, as in FIG. 1, the sulphuric acid and the nitric acid may be previously mixed, requiring two inlets. The second reactor section 14 has an outlet 24 for the removal of the nitration products, e.g., MNB and MNT.

The individual reactor sections 12, 14 are preferably supported at a common elevation. This reduces differences in thermal expansion during operation and avoids the need for flexible piping elements such as expansion joints. However, it may be necessary in some applications to support the individual reactor sections at different elevations.

The reactor 10 can be site assembled. It can be skid mounted to facilitate remote construction and shipment of the completed sections to the site.

The reactor 10 is operated according to the following method. The nitration reactants, for example benzene, sulphuric acid and nitric acid, are fed into the first reactor section 12 and are flowed through the first reactor section 10, the connecting section 16 and the second reactor section 14, under nitrating conditions. Operating conditions within the connecting section, and in particular its down-flow region 26, are selected such that the flow regime in that section is Dispersed flow or Bubbly flow, and/or that the stability parameter is in the interval $0<\Phi \leq 1$. The nitration products, e.g. MNB, are withdrawn from the reactor through the outlet 24.

FIGS. 2(a) to (h) illustrate several alternative embodiments of the nitration reactor 10.

Figure 2A:
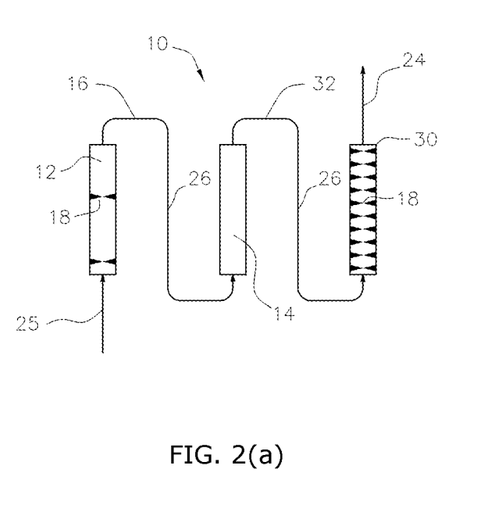
FIGS. 2(a) to (h) are schematic diagrams of nitration reactors according to other embodiments of the invention.

FIGS. 2(a) and (g) illustrate embodiments in which the reactor 10 includes a third reactor section 30 connected in series to the second reactor section 14 by a second connecting section 32 having a region 26 with a vertically-downward flow. The reactor 10 can comprise any suitable number of reactor sections, connected in series, for example five or eight or twenty reactor sections.

A reactor section can have downward flow, instead of only upward flow as in FIG. 1. For example, in FIG. 2(b), the second reactor section 14 has downward flow, and in FIG. 2(e), the first reactor section 12 has downward flow.

Figure 2B:
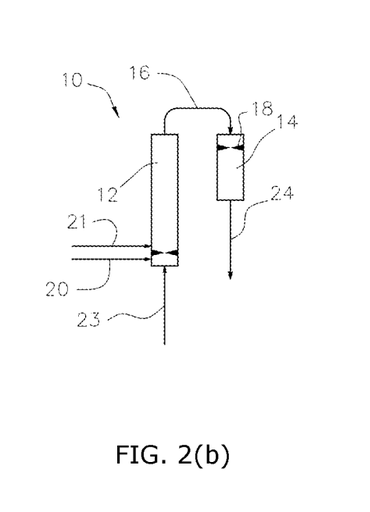

As explained above, the reactants can be introduced individually in three inlets, as shown in FIG. 2(b), with an inlet 20 for the organic stream, an inlet 21 for the sulphuric acid stream and an inlet 23 for the nitric acid stream; or all reactants may be previously mixed, requiring only one inlet 25, as shown in FIGS. 2(a), (e), (f), (g) and (h). Alternatively, the sulphuric acid and organic stream could be previously mixed in inlet 29 and then nitric acid could be added in a separate inlet 27, as shown in FIG. 2(c).

As shown in FIG. 2(a), a reactor section may have no mixing devices or it may have one or more mixing devices 18. Under certain process conditions, the reactor residence time limits the reaction rate and no mixing devices are required in a section of a reactor.

Figure 2C:
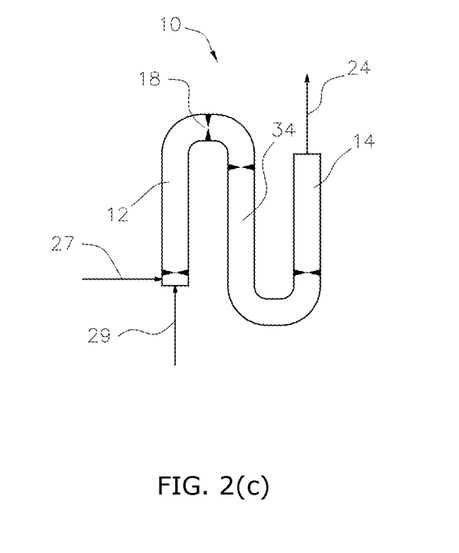

Mixing devices 18 are generally installed in vertical sections 12, 14 of the reactor, but they may be installed in horizontal sections, as illustrated in FIG. 2(c).

As depicted in FIG. 2(c), adjacent reactor sections 12 and 14 with reactants flowing upwards and downwards may be combined by a full-sized connecting section 34, such that the connecting section 34 functions as a reactor section.

Figure 2D:
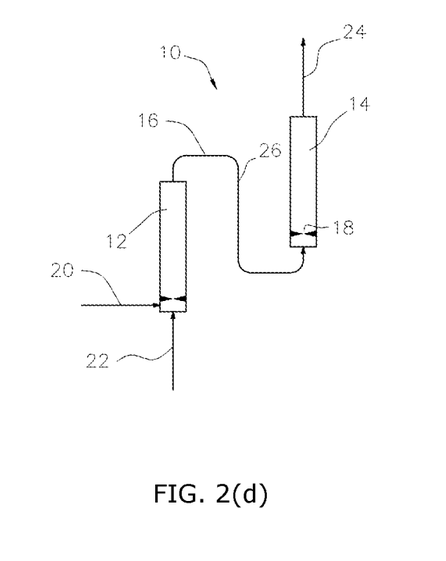

The reactor sections may be installed all at the same elevation, as in FIG. 1, or they may be installed at higher or lower elevations. For example, as illustrated in FIG. 2(d), the second reactor section 14 is at a higher elevation than the first reactor section 12. Here, a portion of the second reactor section 14 has an elevation in common with the first reactor section 12.

The reactor sections 12, 14 may have substantially identical configurations and volumes, as shown in FIG. 1, as this design simplifies manufacturing and assembly. Alternatively, the reactor may be designed with differing reactor sections so as to meet certain process requirements such as minimizing the formation of a specific byproduct. For example, FIG. 2(b) depicts a reactor 10 in which the second reactor section 14 is smaller than the first reactor section 12.

Figure 2E:
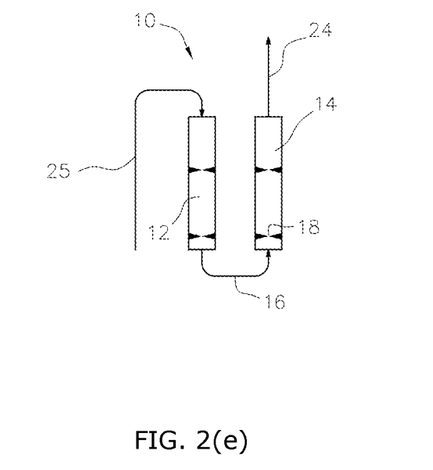

The reactor inlet or inlets may be located on the bottom of the first reactor section as shown in FIG. 1 or may be located on the top of the first reactor section 12 as depicted in FIG. 2(e).

The reactors 10 may include some sections or portions of sections having horizontal flow. For example, FIG. 2(b) shows a portion of the connecting section 16 that is horizontal. Likewise the reactors can include reactor sections that are horizontal. However, it is preferred that the use of horizontal sections is limited, so that more than 50% of the reactor volume is flowing vertically upwards or downwards.

Figure 2F:
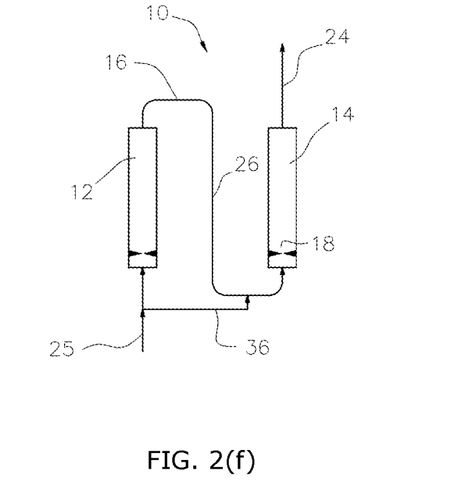
Figure 2G:
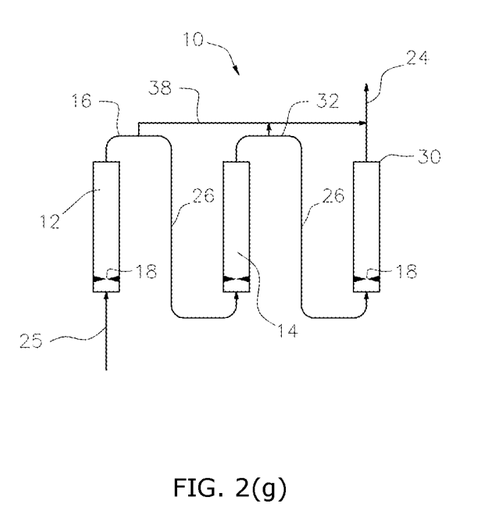
Figure 2H:
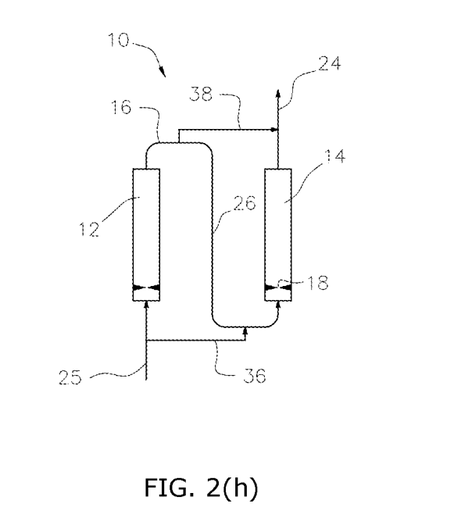

To improve safety during a loss in circulation and to improve stability during startup, vent and drain lines may be installed connecting to one or more reactor sections. These allow gas to be quickly vented during startup and reactants to be quickly drained during shutdown. In the event of a normal shutdown in which the reactor remains flooded the vent and drain lines allow organic material to be purged out of the reactor. FIGS. 2(f) and (h) depict reactors 10 having a draining conduit 36 at the bottom of the reactor. FIGS. 2(g) and (h) depict reactors 10 having a venting conduit 38 at the top of the reactor.

Valves may be installed in the venting and draining conduits to prevent flow through these conduits during operation. Orifices or another flow restriction device may be installed in these conduits to limit bypassing flow during operation and possibly act as a small parallel reactor. Flow in these conduits is generally forward by design, but fluid may occasionally flow against the direction of normal operation during, for instance, reactor draining.

Examples

In a first example, the first downflow section in a nitration reactor conveys a continuous phase consisting of a mixture of sulphuric and nitric acid with $Q_c=0.771$ ft$^3$/s and $\rho_c=95.51$ lb/ft$^3$, and a dispersed phase of mostly benzene with $Q_d=0.056$ ft$^3$/s and $\rho_d=50.91$ lb/ft$^3$ between which exists an interfacial tension of $\sigma=0.055$ lb/s$^2$. The downflow section has perimeter P=1.57 ft, and area A=0.196 ft$^2$. On evaluation, it is found that the downflow section has a hydraulic diameter of D=0.5 ft, and bulk fluid velocity of 4.212 ft/s. It can then be seen that the void fraction, β=0.0677, Eötvös Number, Eo=6,505, and Richardson Number, Ri=0.423. Using these values, the stability parameter, Φ, is found to be 0.355. Using the flow map in FIG. 3, it is predicted that this section of downflow will operate in the 'Bubbly' flow regime, close to the 'Dispersed' flow regime. Note that the units of the physical parameters are canceled such that parameters β, Eo, Ri and Φ are dimensionless.

In a second example, the seventh downflow section in a larger nitration reactor conveys mostly sulphuric acid as the nitric acid has been converted to product with $Q_c=280.9$ m$^3$/hr and $\rho_c=1497$ kg/m$^3$, and a dispersed phase of mostly mononitrobenzene (MNB) with $Q_d=25.3$ m$^3$/hr and $\rho_d=1087$ kg/m$^3$, between which exists an interfacial tension of $\sigma=0.016$ N/m. In this reactor, the downflow section has a square cross-section with perimeter P=1.4 m, area A=0.122 m$^2$, and hydraulic diameter D=0.35 m. Bulk fluid velocity U=0.694 m/s, β=0.0826, Eo=30,784, and Ri=1.95. In this downflow section of the larger reactor, the stability parameter, Φ, evaluates to 0.126. Using FIG. 3, it can be predicted that this downflow section of the reactor will operate in the 'Bubbly' flow regime.

Throughout the foregoing description and the drawings, in which corresponding and like parts are identified by the same reference characters, specific details have been set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

As will be apparent to those skilled in the art in the light of the foregoing disclosure, many alterations and modifications are possible in the practice of this invention without departing from the scope thereof. Accordingly, the scope of the invention is to be construed in accordance with the following claims.

The invention claimed is:

1. A nitration reactor for use in nitrating aromatic organic compounds, comprising:
    (a) a first vertically-oriented reactor section;
    (b) a second vertically-oriented reactor section;
    (c) a connecting section between the first reactor section and the second reactor section for the flow of nitration reactants from the first reactor section to the second reactor section;
    (d) one or more inlets for introduction of the nitration reactants into the reactor;
    (e) an outlet for the removal of nitration reaction products from the reactor;
    (f) a vertically-downward flowpath for the nitration reactants in at least one of the first reactor section, the connecting section and the second reactor section; and
    (g) wherein operating conditions in the section of the reactor having the vertically-downward flowpath are such that a stability parameter Φ is in the interval of 0<Φ≤1, where $$\phi = \frac{\beta}{a \cdot \sqrt{Ri} + b \cdot Eo + c}$$

a=−1.1836×10$^{-1}$
b=2.2873×10$^{-5}$
c=1.1904×10$^{-1}$
Ri=Richardson Number $$Ri = \frac{gD(\rho_c - \rho_d)}{\rho_c U^2}$$

β=volumetric fraction of a dispersed, organic phase, $$\beta = \frac{Q_d}{Q_d + Q_c}$$

Eo=Eötvös Number $$Eo = \frac{(\rho_c - \rho_d)gD^2}{\sigma}$$

U=bulk fluid velocity $$U = \frac{Q_d + Q_c}{A}$$

D=downflow section hydraulic diameter $$D = \frac{4A}{P}$$

A=downflow section cross-sectional area,
P=downflow section cross-sectional perimeter,
g=gravitational acceleration constant,
$\rho_c$=density of continuous phase,
$\rho_d$=density of dispersed phase,
$Q_c$=volumetric flow of continuous phase,
$Q_d$=volumetric flow of dispersed phase, and
σ=interfacial tension.

2. The nitration reactor according to claim 1, wherein the section having the vertically-downward flowpath is the connecting section.

3. The nitration reactor according to claim 1, wherein the section having the vertically-downward flowpath is the first reactor section.

4. The nitration reactor according to claim 1, wherein the section having the vertically-downward flowpath is the second reactor section.

5. The nitration reactor according to claim 1, wherein the first reactor section and the second reactor section have the same configuration.

6. The nitration reactor according to claim 1, wherein the first reactor section and the second reactor section have a different configuration.

7. The nitration reactor according to claim 1, further comprising a plurality of additional vertically-oriented reactor sections and connecting sections connected in series downstream of the second reactor section, at least one of said additional reactor sections and connecting sections having an additional vertically-downward flowpath for the nitration reactants, and the operating conditions produce a flow regime in at least one of the additional vertically-downward flowpaths that is a dispersed flow regime or a bubbly flow regime.

8. The nitration reactor according to claim 1, wherein the section having the vertically-downward flowpath has a cross-section that is circular.

9. The nitration reactor according to claim 1, wherein the section having the vertically-downward flowpath has a cross-section that is non-circular.

10. The nitration reactor according to claim 1, further comprising one or more mixing devices for mixing the nitration reactants.

11. The nitration reactor according to claim 10, wherein at least one said mixing device is positioned within a reactor section having a vertically-downward flowpath.

12. The nitration reactor according to claim 1, further comprising a venting conduit arranged to vent a gas from the reactor.

13. The nitration reactor according to claim 1, further comprising a draining conduit arranged to drain a liquid from the reactor.

14. A method of nitrating an aromatic organic compound using a nitration reactor comprising a first vertically-oriented reactor section, a second vertically-oriented reactor section, a connecting section between the first reactor section and the second reactor section for the flow of nitration reactants from the first reactor section to the second reactor section, and a vertically-downward flowpath for the nitration reactants in at least one of the first reactor section, the connecting section and the second reactor section, the method comprising the steps of:
(a) introducing the nitration reactants into the first reactor section;
(b) flowing the nitration reactants through the first reactor section, the connecting section and the second reactor section under nitrating conditions to produce nitration products;
(c) selecting operating conditions in the section of the reactor having the vertically-downward flowpath such that a stability parameter $\Phi$ is in the interval of $0<\Phi\leq 1$, where $$\phi = \frac{\beta}{a \cdot \sqrt{Ri} + b \cdot Eo + c}$$

$a=-1.1836\times 10^{-1}$
$b=2.2873\times 10^{-5}$
$c=1.1904\times 10^{-1}$
Ri=Richardson Number $$Ri = \frac{gD(\rho_c - \rho_d)}{\rho_c U^2}$$

$\beta$=volumetric fraction of a dispersed, organic phase, $$\beta = \frac{Q_d}{Q_d + Q_c}$$

Eo=Eötvös Number $$Eo = \frac{(\rho_c - \rho_d)gD^2}{\sigma}$$

U=bulk fluid velocity $$U = \frac{Q_d + Q_c}{A}$$

D=downflow section hydraulic diameter $$D = \frac{4A}{P}$$

A=downflow section cross-sectional area,
P=downflow section cross-sectional perimeter,
g=gravitational acceleration constant,
$\rho_c$=density of continuous phase,
$\rho_d$=density of dispersed phase,
$Q_c$=volumetric flow of continuous phase,
$Q_d$=volumetric flow of dispersed phase, and
$\sigma$=interfacial tension; and
(d) removing the nitration products from the nitration reactor.

15. The method according to claim 14, wherein the nitration reactor further comprises a plurality of additional vertically-oriented reactor sections and connecting sections connected in series downstream of the second reactor section, at least one of said additional reactor sections and connecting sections having an additional vertically-downward flowpath for the nitration reactants, and the method further comprises the step of selecting operating conditions in the at least one section of the reactor having the additional vertically-downward flowpath such that a flow regime in said at least one section is dispersed flow or bubbly flow.

16. The method according to claim 14, wherein the section having the vertically-downward flowpath is the connecting section.

17. The method according to claim 14, wherein the section having the vertically-downward flowpath is the first reactor section.

18. The method according to claim 14, wherein the section having the vertically-downward flowpath is the second reactor section.

19. The method according to claim 14, wherein the section having the vertically-downward flowpath has a cross-section that is circular.

20. The method according to claim 14, wherein the section having the vertically-downward flowpath has a cross-section that is non-circular.

21. The method according to claim 14, further comprising one or more mixing devices for mixing the nitration reactants.

22. The method according to claim 21, wherein at least one said mixing device is positioned within a reactor section having a vertically-downward flowpath.

\* \* \* \* \*